United States Patent [19]

Van Kemenade

[11] 4,413,521
[45] Nov. 8, 1983

[54] APPARATUS FOR EXAMINING AN OBJECT BY MEANS OF ULTRASONIC WAVES

[75] Inventor: Martinus J. C. Van Kemenade, Santa Ana, Calif.

[73] Assignee: U.S. Philips Corporation, New York, N.Y.

[21] Appl. No.: 370,780

[22] Filed: Apr. 22, 1982

[30] Foreign Application Priority Data

Apr. 29, 1981 [NL] Netherlands ............. 8102104

[51] Int. Cl.³ .................................. G01N 29/00
[52] U.S. Cl. ............................. 73/626; 128/660
[58] Field of Search ............ 73/625, 626, 628, 633, 73/639; 128/660

[56] References Cited

U.S. PATENT DOCUMENTS

| | | | |
|---|---|---|---|
| 3,817,089 | 6/1974 | Eggleton et al. | 73/625 |
| 4,102,204 | 7/1978 | Kretz | 73/626 |
| 4,143,554 | 3/1979 | Nagy et al. | 73/626 |
| 4,383,447 | 5/1983 | Kretz | 73/626 |

FOREIGN PATENT DOCUMENTS 1089077  11/1980  Canada .............. 128/660

*Primary Examiner*—Howard A. Birmiel
*Attorney, Agent, or Firm*—Jack E. Haken

[57] ABSTRACT

The apparatus comprises a cylindrical carrier (1) which is rotatable about a supporting shaft (5) and is provided with n transducers (3) regularly distributed around its periphery, a first display device (35) for the display of a circular sector scan ultrasonic image with m radial picture lines in the B-mode, and a second display device (37) for an M-mode display of an ultrasonic image which consists of images relating to a single selected picture line (k) of the former image relating to successive instants in time, the successive line images being arranged parallel to one another with the same interline spacing. In order to obtain a line image repetition frequency in the M-mode for the selected picture line (k), which is n times greater than the picture frequency in the B-mode, the device is arranged so that each of the n transducers provides data for the formation of a corresponding group of m/n picture lines during one revolution of the carrier, the transducers taken as a whole together providing the data for all m picture lines. The image is formed in the B-mode by an n-fold line interlace (e.g. FIG. 4 where n=4). Each time any one of the transducers is in a position to provide data concerning the selected picture line (k), the formation of the image in the B mode is interrupted, the relevant transducer is activated to form the selected picture line (k), and transmitter pulses relating to any of the (n−1) lines following the selected line in the numerical sequence of lines, is suppressed.

5 Claims, 4 Drawing Figures

APPARATUS FOR EXAMINING AN OBJECT BY MEANS OF ULTRASONIC WAVES

BACKGROUND OF THE INVENTION

The invention relates to apparatus for examining an object by means of ultrasonic waves.

This invention relates to prior art ultrasonic imaging apparatus which comprises:
(a) a cylindrical carrier which is rotatable on a supporting shaft and is provided with n transducers for the emission and reception of ultrasonic energy, which are regularly distributed along the periphery of the carrier;
(b) a drive motor which is coupled to the shaft;
(c) an annular position sensing device for determining the angular position of the carrier;
(d) a transmitter;
(e) a receiver;
(f) connection means for connecting the transmitter and the receiver to the respective transducers in succession;
(g) a first display device for the display of an ultrasonic image in the B-mode which is arranged to display an image of a scanned region of the object, in the form of a sector of a circle, the image consisting of m picture lines which together span a sector of a circle, the direction of each picture line correspondingly displaying the direction in which the transducer connected to the transmitter and the receiver is directed during the formation of the picture line;
(h) a second display device for the display of an ultrasonic image in the M-mode, which is arranged to display, as a succession, images formed by the same selected picture line and relating to a plurality of successive instants in time, the successive images of the selected picture line being arranged parallel to one another with the same interline spacing;
(i) a switching member for the selective connection of the receiver to the first display device and/or to the second display device;
(j) a control device which is arranged to actuate the transmitter each time the carrier reaches one of a plurality of predetermined angular positions and to control the switching member so that it connects the receiver to the second display device in each angular position of the carrier in which a respective one of the transducers is directed in a direction corresponding to the selected picture line, and such apparatus will be referred to herein as apparatus of the kind set forth.

The first display device in apparatus of this kind displays a two-dimensional image of the object under examination, for example, the heart of a patient. To achieve this, a transducer emits an ultrasonic wave in a given direction and subsequently receives the echo signals produced by acoustic discontinuities at different depths within the object. These echo signals are reproduced as dots on a picture line, the direction of the picture line corresponding to the direction along which the transducer is directed, the location of each dot on the picture line corresponding to the distance between the transducer and the relevant acoustic discontinuity. Shortly thereafter, the carrier will have rotated through a small angle, so that the transducer will then emit in a slightly different direction and, consequently, the next picture line will also have a slightly different direction. The successive picture lines together form an image display in the form of a sector of a circle (B-mode display). Successive images relating to a selected picture line, are formed in the same manner, but are each displayed at a different location, for example, as a series of parallel line images on a strip of paper in a recording apparatus. When given acoustic discontinuities move within the object (for example, cardiac valves), the corresponding dots will each time be situated at a different location on the selected picture line, so that successive images of the selected picture line will give an indication of these displacements (M-mode display).

For an accurate display of the displacements, it is important that the number of successive images of a selected picture line per unit of time, should be comparatively large, for example, more than 100 line images per second. It is not possible to form such a large number of successive images of a selected picture line in one second in known apparatus of the kind set forth. Such prior apparatus comprise, for example, four transducers mounted on the carrier which rotates at a speed of 7.5 revolutions per second. Each transducer is excited by the transmitter m times during each revolution so that an image is formed on the first display device four times per revolution, i.e. at a rate of 30 images per second. Each transducer also supplies the data for the selected picture line once per revolution, so that during each second 30 successive images relating to the selected picture line, are also formed.

SUMMARY OF THE INVENTION

It is an object of the invention to provide an improved apparatus of the kind set forth in which the number of successive images relating to a selected picture line, which are formed per second, is n times greater than the number of complete scanned images per second. In comparison with described known apparatus, for example, 120 successive images of a selected picture line can be formed per second for the same picture frequency of 30 scanned images per second.

According to the invention there is provided apparatus for examining an object by means of ultrasonic waves, comprising:
(a) a cylindrical carrier which is rotatable on a supporting shaft and is provided with n transducers for the emission and reception of ultrasonic energy, which are regularly distributed along the periphery of the carrier;
(b) a drive motor which is coupled to the shaft;
(c) an angular direction sensing device for determining the angular position of the carrier;
(d) a transmitter;
(e) a receiver;
(f) connection means for connecting the transmitter and the receiver to the respective transducers in succession;
(g) a first display device for the display of an ultrasonic image in the B-mode which is arranged to display an image of a scanned region of the object in the form of a sector of a circle, the image consisting of m picture lines which together span a sector of a circle, the direction of each picture line correspondingly displaying the direction in which the transducer connected to the transmitter and the receiver is directed during the formation of the picture line;
(h) a second display device for the display of an ultrasonic image in the M-mode which is arranged to display, as a succession, images formed by the same selected picture line and relating to a plurality of successive instants in time, the successive images of the selected picture line being arranged parallel to one another with the same interline spacing;

(i) a switching member for the selective connection of the receiver to the first display device and/or to the second display device;

(j) a control device which is arranged to actuate the transmitter each time the carrier reaches one of a plurality of predetermined angular positions and to control the switching member so that it connects the receiver to the second display device in each angular position of the carrier in which a respective one of the transducers is directed in a direction corresponding to the selected picture line, characterized in that the control device is arranged to actuate the transmitter according to a cycle in which each of the n transducers supplies the data for the formation of a corresponding group of m/n picture lines (i.e. during one revolution of the carrier the transducers taken as a whole would supply the data for the m picture lines), said cycle being interrupted for an interrupt period during which a respective operative transducer occupies a position in which it would otherwise supply data for anyone of the n-1 picture lines which directly follow the selected picture line (k) in the numerical sequence of lines the transmitter being actuated at every instant at which any transducer occupies a position in which it can supply data for the selected picture line (k).

DESCRIPTION OF THE DRAWINGS

An embodiment of the invention will now be described by way of example, with reference to the accompanying drawings, of which.

DESCRIPTION OF THE PREFERRED EMBODIMENT

Figure 1:
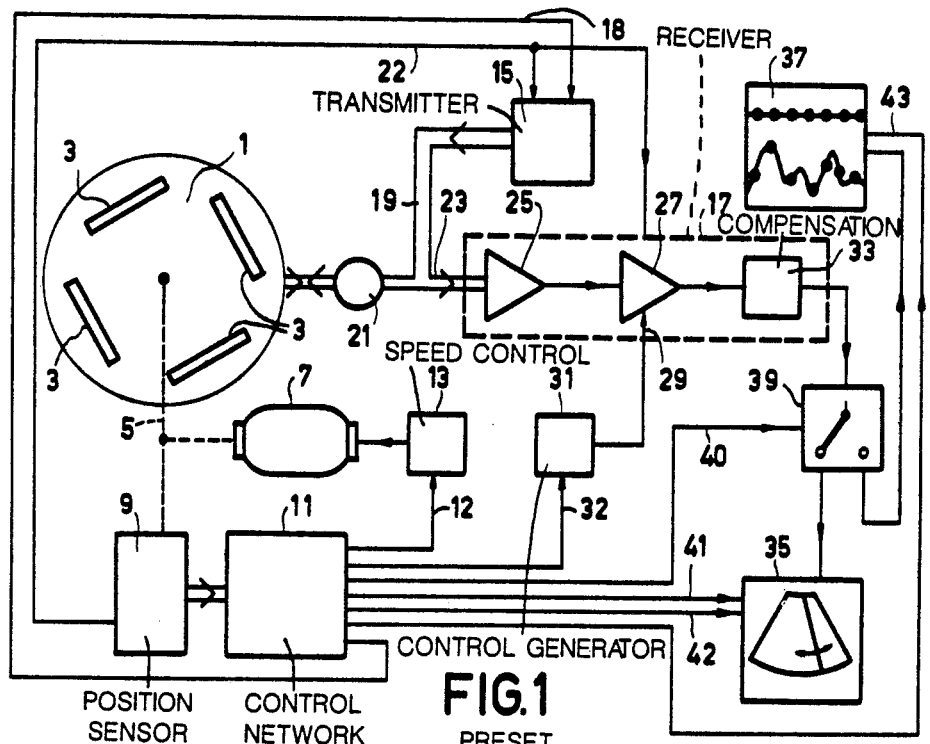
FIG. 1 is a block diagram of an embodiment of apparatus in accordance with the invention.

Apparatus embodying the invention is shown in the form of a block diagram in FIG. 1, and comprises a cylindrical carrier 1 which is mounted on and rotatable about a supporting shaft illustrated diagrammatically by 5, and is provided with four transducers 3 for emitting and receiving ultrasonic energy, regularly distributed around the peripheral surface of the carrier 1. Thus, in this example n which is used herein to represent the number of transducers, equals four. The transducers are formed, for example, by plates of a piezo-electric material with corresponding electrodes. The shaft 5 of the carrier 1 (denoted by a broken line) is coupled to a drive motor 7 and to an angular position sensing device 9 for determining the angular position of the carrier. The angular position sensing device 9 and a control device 11 connected thereto will be further described hereinafter with reference to FIG. 2 in as far they are of relevance to a proper understanding of the present invention. The control device 11 also has a number of known functions, such as controlling a speed controller 13 for the drive motor 7 via a lead 12.

The apparatus further includes a transmitter 15 and a receiver 17. The transmitter 15 comprises four high frequency generators of known kind, each of which is arranged to excite the transducer 3 for a brief period of time after the reception of a start pulse which is generated by the control device 11 and which is applied via a lead 18. Because of the use of four generators, each transducer 3 can be assigned uniquely to a corresponding generator and the properties of the transducer and the associated generator can be optimally matched. A further advantage of the use of four generators is that when the connection between a generator and the associated transducer is broken, the connection between the next transducer and the corresponding generator can already have been established, so that no down time is required for switching from one transducer to the next. The transmitter 15 is connected, via a transmission cable 19, to slip rings 21 which serve as connection means for respectively connecting the transmitters and the receivers to a corresponding one of the transducers 3. Thus, each transducer 3 is connected to the corresponding transmitter and receiver, so that it is operative, for approximately one quarter of a revolution of the carrier 1. During this period, the respective transmitter and receiver and the corresponding operative transducer are used to scan a region of the object, which has the form of a sector of a circle. Subsequently, the next transducer is rendered operative and together with its related transmitter and receiver is used to scan the same region of the object, etc. The transmitter 15 and the receiver 17 receive, via a lead 22, a signal which is generated by the angular position sensing device 9 and which indicates which of the transducers 3 is to be made operative.

The slip rings 21 are also connected, via a receiver cable 23, to four preamplifiers 25 which form part of the receiver 17. Each preamplifier 25 is optimally matched to the properties of the corresponding one of the four transducers 3. It will be apparent that the selection of the appropriate one of the four preamplifiers can be effected in a similar manner to the selection of one of the four generators forming the transmitter 15, by means of the signal applied via the lead 22.

The receiver 17 further includes a controllable amplifier 27 whose gain is controlled by a control voltage which is applied via a control input 29 and which originates from a control voltage generator 31 which is actuated by the control network 11 via a lead 32. This facility is known per se and ensures that after the emission of an ultrasonic wave by the operative transducer 3 the gain of the amplifier 27 is gradually increased with time in order to compensate for the correspondingly decreasing intensity of the echo signals received from greater depths. Such a decrease is due to the fact that the echo signals received later will have travelled further through the object under examination. The controllable amplifier 27 is followed by a known compensation circuit 33 for adaptation of the dynamic range of the signals to the ratio of the maximum to the minimum brightness which can be usefully displayed by a display device connected to the receiver 17.

The apparatus shown in FIG. 1 includes two of such display devices, namely a first display device 35 for the display of an ultrasonic image in the B mode, and a second display device 37 for the display of an ultrasonic image in the M-mode. The apparatus further includes a switching member 39 for selectively connecting the receiver 17 to the first display device 35 and/or to the second display device 37. This switching member is controlled by the control device 11 via a lead 40.

The first display device 35 includes a display screen on which the image is displayed in the form of a sector of a circle consisting of 128 picture lines which form the radii of the sector. Thus, in this example m is 128. The direction of each of these picture lines corresponds to the direction in which the transducer 3 connected to the transmitter and the receiver 15, 17 (the operative transducer) is directed during the formation of that picture line. Each echo signal received by the transducer is displayed as a luminescent dot on the picture line, the dots being situated further from the centre of the circular sector as they are received later by the transducer, i.e. as they originate from regions lying deeper within the object under examination. The image on the display screen is thus a representation of the structure of the sector shaped region of the object under examination which is successively scanned by the respective operative transducers 3 connected to the corresponding transmitters and receivers.

The information concerning the brightness of the image at any instant, therefore, originates from the receiver 17. When the position of the switching member 39 is such that no brightness information is supplied from the receiver 17 to the first display device 35, the brightness displayed thereby is controlled by the control device 11 via a lead 42. The information concerning the image scan, that is to say the coordinates of the luminescent image dots on the display screen, is provided by the control device 11 and is applied to the first display device 35 via a lead 41.

The second display device 37 comprises, for example, a recording apparatus for recording the received signal on paper which is sensitive to ultraviolet light by means of an ultraviolet light beam originating from a printing head (ultraviolet recorder). Each time one of the transducers 3 reaches a position in which it can transmit and receive in the direction corresponding to a previously selected picture line, the control device 11 instructs the switching member 39 to connect the receiver 17 to the second display device 37. A straight line is then scanned on the paper of this display device, a dot being written each time an echo signal is received by the receiver 17. The location of the dot on the line will depend on the instant at which the echo is received, and this location information will be passed from the main control device 11 via a lead 43. It will be apparent from the foregoing that the line displayed by the second display device 37 will contain the same information as a picture line as is actually the selected picture line. The switching member 39 may be arranged so that the selected picture line is only displayed on the second display device 37, whilst the brightness of the first display device 35 is maintained at a constant value via the lead 42. However, it is alternatively possible to adapt the switching member 39 so that the selected picture line is displayed on both the first display device 35 and on the second display device 37.

The paper of the ultraviolet recorder of the second display device 37 is moved at a constant low speed (for example, 25 mm/s) with respect to the printing head in a direction perpendicular to the direction in which the selected picture line is recorded. Successive selected picture lines are thus imaged in parallel with a uniform spacing. If the object under examination contains moving structures, the echo signals from these structures will be situated at different locations on successive images of the selected picture lines, so that the image formed is a representation of the displacement (M-mode) when it is read perpendicularly to the direction of the image lines.

Figure 2:
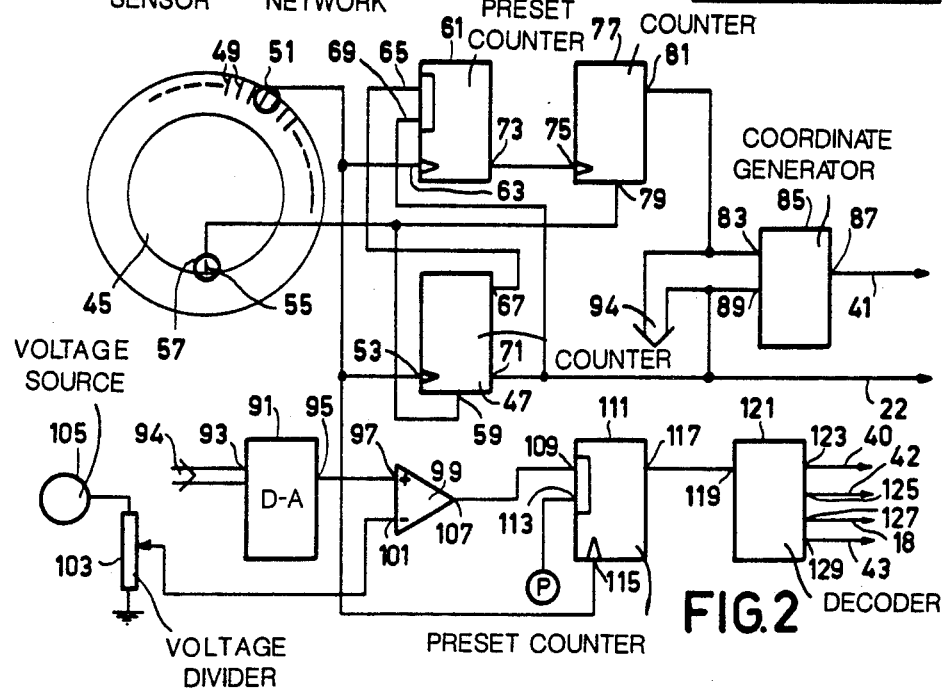
FIG. 2 is a more detailed block diagram of a part of the embodiment shown in FIG. 1.

FIG. 2 shows a block diagram of an embodiment of a circuit comprising the angular position sensing device 9 and the control device 11. The angular position sensing device 9 includes a disc 45 which is mounted on the shaft 5 of the carrier 1 and a 512-counter 47. The disc 45 comprises m.n=512 marks 49 which are regularly distributed around its periphery, for example, slits in the otherwise opaque peripheral edge of the disc. Passage of one of these marks past a reference position, is detected by means of a first detector 51, comprising, for example, a light source on one side of the disc 45 and a light-sensitive element on the other side. The pulses supplied by the first detector 51 in response to passage of the marks 49 past the reference position defined thereby, are applied to the counting input 53 of the 512-counter 47. The disc 45 is further provided with a single mark 55 which is situated radially inwards of the annular region occupied by the marks 49, and may be of the same form as these marks. Passage of the mark 55 past a corresponding reference position, is detected by means of a second detector 57 which may take the same form as the first detector 51. The pulses thus supplied are applied to the reset input 59 of the 512-counter 47. Thus, each time the mark 55 passes the second detector 57, the 512-counter is reset to zero and then counts the marks 49 passing the first detector 51. The count present in this counter thus indicates the angular position of the carrier 1.

The other parts shown in FIG. 2 belong to the control device 11. A presettable 4-counter 61 has its counting input 63 connected to the first detector 51. The "load" instruction input 65 of this counter is connected to a first output 67 of the 512-counter 47 on which a signal appears after each count of 128 pulses. The presetting data input 69 of the presettable 4-counter 61 is connected to a second output 71 of the 512-counter 47 on which the two most-significant bits of the count present in this counter appear; these bits are also applied to the transmitter 15 and the receiver 17 via the lead 22. The output 73 of the presettable 4-counter 61 is connected to the count input 75 of a 32-counter 77, the reset input 79 of which is connected to the second detector 57. The output 81 of the 32-counter 77 is connected to a first input 83 of a coodinate generator 85 whose output 87 is connected to the first display device 35 via the lead 41 (FIG. 1). A second input 89 of the coodinate generator 85 is connected to the second output 71 of the 512-counter 47.

A digital-to-analog converter 91 is provided with an input 93 which is connected, via a cable 94, to the output 81 of the 32-counter 77 and the second output 71 of the 512-counter 47. For the sake of clarity in the figure, the cable 94 is not shown in its entirety. The digital-to-analog converter 91 is provided with an output 95 which is connected to a first input 97 of a comparator 99 whose second input 101 is connected to the adjustable tap of an adjustable voltage divider 103 which is connected between a voltage source 105 and ground. The output 107 of the comparator 99 is connected to the "load" input 109 of a presettable 128-counter 111 whose presetting data input 113 receives a fixed value P. The value P is, for example, equal to the number 4 in binary form. The count input 115 of the presettable 128-counter 111 is connected to the first detector 51 and its output 117 is connected to the input 119 of a decoder 121 which is provided with four outputs. The first output 123 is connected to the lead 40 which is connected to the switching member 39; the second output 125 is connected to the lead 42 which is connected to the first display device 35; the third output 127 is connected to the lead 18 which is connected to the transmitter device 15; and the fourth output 129 is connected to the lead 43 which is connected to the second display device 37.

The operation of the circuit shown in FIG. 2 is as follows. The disc 45 rotates at the same rotational speed as the carrier 1, so that during each revolution of the carrier one pulse is supplied by the second detector 57 and 512 pulses are supplied by the first detector 51. The pulses supplied by the second detector 57 are applied to the reset inputs 59 and 79 of the 512-counter 47 and the 32-counter 77, respectively. Thus, both counters will be reset to zero once per revolution.

The pulses supplied by the first detector 51 are applied to the count input 53 of the 512-counter 47, the count input 63 of the presettable 4-counter 61 and the count input 115 of the presettable 128-counter 111. The count present in the 512-counter 47 will thus gradually increase from zero to 512 during one revolution, after which it is restarted from zero. The two most-significant bits of this count, indicating which one of the four transducers is to be rendered operative, are applied inter alia to the lead 22 and to the presetting data input 69 of the presettable 4-counter 61. Furthermore, each time the counter 47 is reset to zero or each succession of 128 pulses have been counted, i.e. for each quarter of a revolution of the carrier 1, the 512-counter 47 applies a signal to the "load" input 65 of the presettable 4-counter 61, so that after each quarter of a revolution this counter is loaded with an initial count value which indicates the sequence number of the transducer 3 which is then operative. Starting from this value, the counter 61 counts the pulses from the first detector 51 until it reaches a count of 4, after which it starts counting again from zero. Each time the counter 61 returns to zero, it applies, via the output 73, a pulse to the count input 75 of the 32-counter 77, the count of which is reset to zero once per revolution via the reset input 79. The binary digits representing the count in the 32-counter 77 are applied in a similar manner to the digits representing the two most-significant bits of the count in the 512 counter and which latter indicate the sequence number of the operative transducer, to the coordinate generator 85 and, via the cable 94, to the digital-to-analog converter 91.

Thus, the binary number applied to the coordinate generator 85 consists of a total number of seven bits, i.e. the two bits indicating the sequence number of the transducer (varying from zero to three) and five bits from the 32-counter which indicate a number which varies from zero to 31. The value of the binary number applied to the coordinate generator 85 thus varies from 0 to 127, each value corresponding to the sequence number of one of the 128 picture lines which together form the circular sector image on the first display device 35. It should be noted, however, that the two bits indicating the sequence number of the transducer and applied to input 89, must be arranged in the coordinate generator 85 to form the two least significant digits of the sequence number thus formed. This is because the presettable 4-counter 61 start is arranged to start to count at the sequence number of the relevant transducer each time the next transducer is rendered operative, and the sequence numbers of the 128 picture lines must therefore be applied to the coordinate generator 85 in the sequence: 0, 4, 8, ..., 124, 1, 5, 9, ..., 125, 2, 6, 10, ..., 126, 3, 7, 11, ..., 127. Thus, during the operative state of one of the four transducers, a group comprising a quarter of the total number of picture lines will be formed, and a corresponding group comprising a different quarter of the total number of picture lines will be associated with each respective transducer, each group comprising an interlacing sequence of lines. When all the transducers have been rendered operative once, i.e. after one revolution of the carrier, therefore, all of the 128 picture lines will have been formed. The coordinate generator 85 is arranged to generate for each sequence number relating to a picture line, a signal which causes the first display device 35 to scan the corresponding picture line on its display screen. To achieve this, the coordinate generator 85 may comprise a read only memory with 128 addresses each storing the corresponding scan parameters. The signal generated is applied to the first display device 35 via the lead 41.

The input 93 of the digital-to-analog converter 91, also receives the five bits of the count output from the 32-counter 77 and the two most-significant bits of the count from the 512-counter 47, which together form a number which corresponds to the number applied to the coordinate generator 85, and to the sequence number of one of the 128 picture lines. This number thus indicates which picture line is being formed at a given instant.

The sequence number applied to the digital-to-analog converter is converted into an analog voltage which is applied to the first input 97 of the comparator 99. The second input 101 of the comparator receives a predetermined voltage which can be adjusted by means of the voltage divider 103 and whose value is made to correspond to that relating to a second picture line. At the instant at which the voltage corresponding to the sequence number equals the predetermined voltage, the comparator applies a signal to the "load" input 109 of the presettable 128-counter 111, with the result that the initial count in the counter 111 becomes equal to the value P (for example, four) applied to its presetting data input 113. Starting from this value, the counter 111 counts the pulses from the first detector 51 until it reaches the value 127, after which it returns to zero. The count in the presettable 128-counter 111 thus indicates the numerical sequence number of the picture line which would be formed at any instant, and when this count equals the value originally present on the data input 113, the picture line due will be the one selected by means of the voltage divider 103. The count in the presettable 128-counter 111 is applied to the input 119 of the decoder 121 in which the value P is also stored. The decoder 121 is arranged to generate various different signals in relation to the selected and associated adjacent picture lines. On the first output 123 a signal is presented which controls the switching member 39 so that it connects the receiver 17 to the second display device 37 only when the selected picture line is due, and to the first display device 35 at all other times. As has already been stated, the connection between the receiver 17 and the first display device 35 can also be maintained, if desired, during the formation of the selected picture line. On the second output 125 a signal is presented which is employed to maintain the brightness of the image displayed on the first display device 35 at a predetermined constant value during the formation of the selected picture line when the selected picture line itself is not to be displayed on the first display device. On the third output 127 a signal is presented which actuates the transmitter 15 at the beginning of each permitted picture line associated with the transducer which is operative at that instant. This signal is also presented at the beginning of the selected picture line, regardless of which transducer is operative at that instant. The selected picture line, therefore, is formed four times per revolution of the carrier 1. On the other hand, the signal on the output 127 must be omitted at the beginning of a picture line in the immediate vicinity of the selected picture line when this would otherwise cause a pulse to be transmitted during the reception period associated with the selected line. This will be elaborated hereinafter with reference to FIG. 3.

Finally, on the fourth output 129 a signal is presented at the beginning of each selected picture line as a start signal for the second display device 37. When this signal is received, the recording head of this display device is set in motion. This display device may comprise a memory in which the brightness information of the selected picture line, originating from the receiver, is stored in response to the start signal. During the wait period before the next occurrence of the selected picture line, this memory can be read several times and the selected picture line correspondingly displayed or written by the second display device. Thus, a better recording density can be obtained on the ultraviolet-sensitive paper of the display device.

Figure 3:
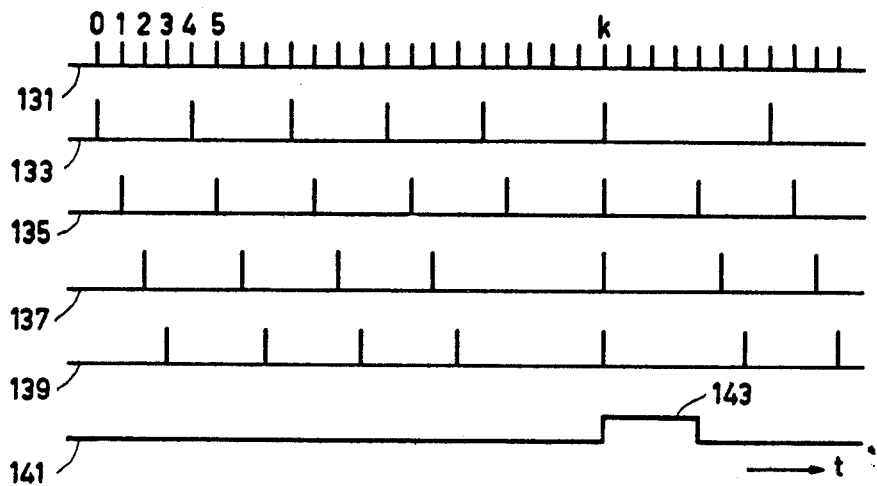
FIG. 3 is a time sequence and pulse waveform diagram relating to the operation of the embodiment, and FIG. 4 diagrammatically illustrates the operation of the embodiment.

FIG. 3 shows a time sequence and pulse waveform diagram illustrating the described procedure during operation of the device. On the top line there is shown a waveform 131 comprising a succession of pulses from the first detector 51, above which there are written the sequence numbers of the associated picture lines. The sequence number of the selected picture line to be displayed by the device 37, is denoted by the letter k. The interval between two successive pulses is 64 $\mu$s; this corresponds to a speed of revolution of the carrier 1 of approximately 30 revolutions per second.

On the next line a waveform 133 shows the instants at which transmission pulses are applied to the first transducer 3 (namely the transducer having the sequence number 0) by the transmitter device 15. On the third line a waveform 135 indicates the instants at which transmission pulses are applied to the second transducer 3 (i.e. having the sequence number 1). On the fourth line a waveform 137 and on the fifth line a waveform 139 indicate the corresponding instants for the third and the fourth transducer, respectively (namely transducers having the sequence numbers 2 and 3). It is to be noted that the waveforms 133, 135, 137 and 139 in fact succeed one another in time sequence. This is because initially the first transducer is rendered operative and transmits at the beginning of the picture lines numbered 0, 4, 8, . . . , 124. Subsequently, the second transducer is rendered operative and transmits at the beginning of the picture lines numbered 1, 5, 9, . . . , 125, followed by the third transducer (picture lines numbered 2, 6, 10, . . . , 126) and finally the fourth transducer (picture lines numbered 3, 7, 11, . . . , 127). Even though the distance between the positions of successive picture lines in the numerical sequence, is covered by the carrier 1 in 64 $\mu$s, in fact a time period of $4 \times 64 = 256$ $\mu$s is available for transmission and subsequent echo reception during the formation of each of the picture lines. The four waveforms 133, 135, 137 and 139 are situated one below the other in FIG. 3 for the sake of clarity in the figure. For example, it is clearly shown that in the case of all the transducers, the operative transducer always transmits at the beginning of the selected picture line k. As has already been stated, during the formation of this picture k, a signal originating from the second output of the decoder 121 is applied, if desired, to the first display device 35 in order to maintain the brightness of the image at a constant value. This signal is shown by the waveform 141 on the last line, in the form of a pulse 143 having a duration of 256 $\mu$s. It will be clear that this signal will be presented each time one of the transducers reaches the position which corresponds to that of the selected picture line k, i.e. four times per revolution of the carrier 1.

FIG. 3 also shows that the cycle during which the transducers are rendered operative in order to provide the data for one quarter of the total number of picture lines, is interrupted in the present embodiment, for each period during which the operative transducer occupies a position in which it would otherwise supply data for any one of the picture lines k−3 to k+3. During this interrupt period the corresponding transducer is excited and rendered operative in the described manner at the instant at which it is in a position to provide data concerning the selected picture line k. This means that the picture lines k−3 to k+3 will not be displayed by the first display device 35. This small loss of information is offset, however, by the large gain of information achieved by the more frequent M-mode display of the selected picture line k. However, the loss of information can be reduced by actuating the corresponding transducers when they are in a position to provide data concerning the picture lines k−3, k=2 and k−1. The normal period of 256 $\mu$s will not be available for the formation of these picture lines, the corresponding period being 192 $\mu$s, 128 $\mu$s and 64 $\mu$s, respectively. For this reason, these picture lines will be incomplete and will only provide information concerning parts of the object under examination which are not situated very deeply therein.

Figure 4:
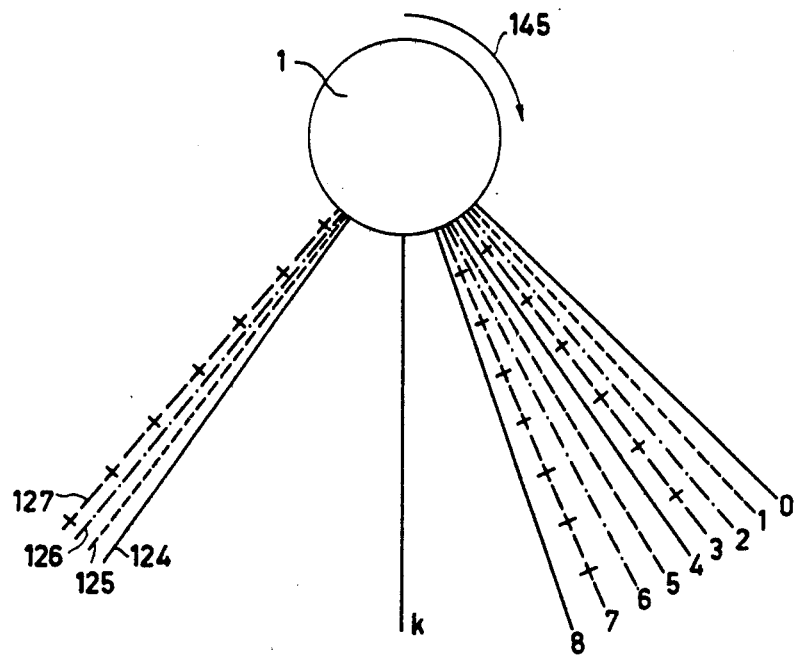

FIG. 4 is a diagram illustrating the carrier 1 and the directions in which the various transducers (not themselves shown) emit in order to obtain the data for the various picture lines. The carrier 1 rotates at a speed of 30 revolutions per second in the direction of the arrow 145. The directions in which the transducers emit are indicated by the numerical sequence numbers of the associated picture lines. The emission directions of the first transducer are denoted by solid lines, those of the second transducer by broken lines, those of the third transducer by stroke dot lines and those of the fourth transducer by stroke cross lines. The direction of the selected picture line k, for which all the transducers emit, is denoted by a solid line.

It will be apparent that, within the scope of the invention claimed, alternative versions of the described embodiment are feasible. For example, a different number of transducers or a different number of picture lines may be chosen. Moreover, the angular direction sensing device shown in FIG. 2 and the control device may have a different construction. A part of their functions could be taken over, for example, by a microprocessor. It is also to be noted that a number of known parts which are not important for a proper understanding of the present invention have been omitted for the sake of clarity. Among these parts are, for example, a generator for generating the control signal applied to the speed controller 13 via the lead 12 and a generator for the signal applied to the control voltage generator 31 via the lead 32.

What is claimed is:

1. Apparatus for examining an object with ultrasonic waves comprising:
   a rotatable shaft;
   a cylindrical carrier supported on the shaft for rotation therewith;
   a group of n transducers, which function to emit and receive ultrasound energy, regularly distributed around the periphery of the carrier;
   drive motor means which function to rotate the shaft;
   angle sensing means which function to determine the angular position of the carrier;
   a transmitter;
   a receiver;
   connecting means which function to successively connect the transmitter and receiver to respective transducers;
   first display means which function to display an image in the B-mode by displaying an image of a scanned region of the object in the form of a sector of the circle wherein the image consists of a sequence of m picture lines which together span the sector of the circle and the direction of each picture line corresponds to the angular position of the transducer which is connected to receiver during receipt of information which is displayed on that picture line;
   second display means which function to display an image in the M-mode by displaying a succession of images formed from a single selected picture line at a plurality of successive instances in time wherein the successive images of the selected picture line are displayed parallel to one another with a constant interline spacing;
   switching means which function to selectively connect the receiver to the first display means and/or to the second display means; and
   control means which function to actuate the transmitter for the transmission of ultrasound energy each time the carrier reaches one of a plurality of predetermined angular positions and to control the switching means so that it connects the receiver to the second display means at each angular position of the carrier in which a respective one of the transducers is aligned in a direction which corresponds to the selected picture line;
   wherein, as an improvement, the control means functions to actuate the transmitter in a cyclic manner so that each of the n transducers supplies data for the formation of a corresponding group of m/n picture lines so that during one revolution of the carrier the entire group of transducers supplies data for m picture lines, to interrupt the cycle for an interrupt period during which a respective operative transducer occupies a positin in which it would otherwise supply data for any one of the n-1 picture lines which immediately follow the selected picture line in the sequence of lines, and to actuate the transmitter at every instant at which any of the transducers occupies a position in which it can supply data for the selected picture line.

2. Apparatus as claimed in claim 1, wherein the interrupt period also includes any one of the n-1 picture lines which directly precede the selected picture line in the sequence of lines.

3. Apparatus claimed in claim 1 or claim 2, wherein the angle sensing means functions to generate a sequence of m.n pulses for each revolution of the carrier, wherein the apparatus further includes a first counter connected to count the pulses in the sequence, and wherein the control means functions to actuate the transmitter in response to the generation of pulses having sequence numbers $0, n, 2n, 3n, \ldots, m-n, m+1, m+1+n, n+1+2n, \ldots, 2m+1-n, 2m+2, 2m+2+n, 2m+2+2n, \ldots$, and in response to the generation of pulses having the sequence number $k+i$, in which k is a selected value and $i=0, m, 2m, \ldots$, but not in response to the generation of pulses having the sequence numbers $k+i+1, k+i+2, \ldots, k+i+n-1$.

4. Apparatus as defined in claim 1 or 2 wherein $n=4$ and $m=128$.

5. Apparatus of claim 3, wherein $n=4$ and $m=128$.

* * * * *